(12) United States Patent
Yamamoto et al.

(10) Patent No.: US 9,173,727 B2
(45) Date of Patent: Nov. 3, 2015

(54) SHADE GUIDE, METHOD FOR DISCRIMINATING TOOTH COLORS, ARTIFICIAL TOOTH MANUFACTURING METHOD

(75) Inventors: Makoto Yamamoto, Osaka (JP); Ryuichi Yosimoto, Kyoto (JP); Noriyuki Negoro, Kyoto (JP); Masuhito Yasui, Kyoto (JP); Kouji Shou, Kyoto (JP)

(73) Assignee: SHOFU INC., Kyoto (JP)

( * ) Notice: Subject to any disclaimer, the term of this patent is extended or adjusted under 35 U.S.C. 154(b) by 377 days.

(21) Appl. No.: 12/667,794

(22) PCT Filed: Jul. 6, 2007

(86) PCT No.: PCT/JP2007/063603
§ 371 (c)(1),
(2), (4) Date: Jan. 5, 2010

(87) PCT Pub. No.: WO2009/008044
PCT Pub. Date: Jan. 15, 2009

(65) Prior Publication Data
US 2010/0173257 A1    Jul. 8, 2010

(51) Int. Cl.
*A61C 19/10*    (2006.01)
*A61C 5/10*    (2006.01)
*A61C 5/00*    (2006.01)

(52) U.S. Cl.
CPC . *A61C 19/10* (2013.01); *A61C 5/10* (2013.01); *A61C 5/002* (2013.01)

(58) Field of Classification Search
CPC .. A61C 19/10; A61C 2201/002; A61C 19/04; G01J 3/00
USPC .................................. 433/26, 25, 203.1, 215
See application file for complete search history.

(56) References Cited

U.S. PATENT DOCUMENTS 3,956,827 A    5/1976  Bergen
5,004,417 A *  4/1991  Giaramita ..................... 433/26
(Continued)

FOREIGN PATENT DOCUMENTS

| JP | 6-233784 | 8/1994 |
| JP | 11-262497 | 9/1999 |
| JP | 3100809 | 8/2000 |

OTHER PUBLICATIONS

Sproull, "Color matching in dentistry, Part II, Practical applications of the organization of color", Journal of Prosthetic Dentistry, vol. 26, No. 5, May 1973, pp. 556-566, XP009089467, ISSN: 0022-3913.

*Primary Examiner* — Yogesh Patel
(74) *Attorney, Agent, or Firm* — Hamre, Schumann, Mueller & Larson, P.C.

(57) ABSTRACT

In a shade guide, a plurality of shade tabs whose colors are mutually different are arranged regularly based on the colors. The arrangement of the plurality of shade tabs is an arrangement determined based on: S values and V values that are determined according to to which areas, from among areas partitioned by a plurality of straight lines in an L*-C* plane, the coordinates of the colors of the shade tabs belong, and H values that are determined according to to which areas, from among areas partitioned by a plurality of straight lines in an a*-b* plane, the coordinates belong. S groups, each of which is a shade tab group having a common S value, are arranged in the shade guide. V rows, each of which is a shade tab group having a common V value, are arranged in each S group. In each V row, the plurality of shade tabs have mutually different H values and are aligned in an order that is in accordance with the H values. Using this shade guide enables precisely and easily discriminating the color of an evaluation target tooth.

3 Claims, 7 Drawing Sheets

(56) References Cited

U.S. PATENT DOCUMENTS

| | | | |
|---|---|---|---|
| 5,149,267 A * | 9/1992 | Longhini et al. | 433/26 |
| 5,261,815 A * | 11/1993 | Pozzi | 433/26 |
| 5,498,157 A | 3/1996 | Hall | |
| 5,685,717 A | 11/1997 | Kramer | |
| 5,904,481 A * | 5/1999 | Shima | 433/26 |
| 6,030,209 A * | 2/2000 | Panzera et al. | 433/26 |
| 6,315,554 B1 * | 11/2001 | Coste | A61C 19/10 433/26 |
| 6,328,563 B1 * | 12/2001 | Hobo | A61C 19/10 433/26 |
| 6,328,567 B1 * | 12/2001 | Morris et al. | 433/215 |
| 7,128,572 B2 * | 10/2006 | Lauciello | A61C 19/10 433/26 |
| 7,303,391 B1 * | 12/2007 | Alexander | A61C 19/10 433/203.1 |

\* cited by examiner

SHADE GUIDE, METHOD FOR DISCRIMINATING TOOTH COLORS, ARTIFICIAL TOOTH MANUFACTURING METHOD

TECHNICAL FIELD

The present invention relates to a shade guide used as a color sample when discriminating the color of a tooth.

BACKGROUND ART

People who have beautiful teeth tend to have a favorable impression on others. Demand for aesthetics with respect to teeth has therefore being increasing year by year. In medical treatment and cosmetic treatment in dentistry, when providing a patient's teeth with a prosthetic such as a denture or a crown restoration, the color of the prosthetic is preferably the same color as the adjacently located teeth. It is therefore required in the manufacturing of the prosthetic to precisely discriminate the color of a patient's tooth and manufacture the prosthetic based on the discriminated color. Note that discriminating the color of a tooth in this way is sometimes called tooth-color evaluation (shade taking).

Conventionally, shade guides have been used as color samples for discriminating the color of teeth. A shade guide has a plurality of shade tabs that are a plurality of colors and are arranged according to the colors. Each shade tab is, for example, formed from plastic and shaped as a tooth. Also, each shade tab has been assigned a number for specifying the color of the shade tab.

For example, an observer brings at least one of the shade tabs close to the patient's tooth, and compares the color of the patient's tooth and the color of the shade tab. As a result of the comparison, the observer selects the shade tab whose color is felt to be the closest to the patient's tooth, and discriminates the color of such shade tab as the color of the patient's tooth. Thereafter, for example, the observer notifies a prosthetics manufacturer of the number that specifies the color of the selected shade tab. The prosthetics manufacturer manufactures a prosthesis using materials that give off the same color as the color specified by the number.

In this way, the discrimination of the color of a tooth includes a subjective evaluation by an observer. Subjective evaluations by observers are different from individual to individual, and vary according to the environment at the time of observation. The reliability of the tooth color discrimination result is prone to being low. There is desire for a shade guide that, in order to improve the reliability of the discrimination result, enables a precise discrimination of the color of a tooth by an observer.

The range of colors of shade tabs in conventional shade guides has not covered the range of colors observed for natural teeth. For this reason, there have been cases in which a color close to the color of a tooth targeted for evaluation cannot be found in the shade guide. In order to address this problem, there has been a proposal for a shade guide in which shade tabs whose colors correspond to the distribution range of the colors of natural teeth specified in a color space are arranged (e.g., see Japanese Patent No. 3100809).

However, the above-described conventional shade guide does not take into account visual sensitivity in the actual perception of colors by humans. This shade guide is therefore insufficient for precisely and easily visually discriminating the color of a tooth targeted for evaluation.

DISCLOSURE OF INVENTION

Problem to be Solved by the Invention

An object of the present invention is to provide a shade guide for precisely and easily visually discriminating the color of an evaluation target tooth.

Means for Solving Problem

A shade guide according to the present invention is a shade guide in which a plurality of shade tabs whose colors are mutually different are arranged regularly based on the colors, the arrangement of the plurality of shade tabs being an arrangement determined based on: S values that, in a case in which the colors of the shade tabs are expressed by coordinates in an $L^*a^*b^*$ color system, are determined according to to which areas, from among areas partitioned by a plurality of straight lines having a predetermined slope k ($0<k$) in an $L^*$-$C^*$ plane, the coordinates belong; V values that, in a case in which the colors of the shade tabs are expressed by coordinates in the $L^*a^*b^*$ color system, are determined according to to which areas, from among areas partitioned by a plurality of straight lines having a predetermined slope m ($0>m$) in the $L^*$-$C^*$ plane, the coordinates belong; and H values that, in a case in which the colors of the shade tabs are expressed by coordinates in the $L^*a^*b^*$ color system, are determined according to to which areas, from among areas partitioned by a plurality of straight lines in an $a^*$-$b^*$ plane, the coordinates belong, a plurality of S groups being arranged, each S group being a shade tab group of shade tabs whose colors have a common S value, a plurality of V rows being arranged in each S group, each V row being a row in which a shade tab group of shade tabs whose colors have a common V value are aligned, and in each V row, the plurality of shade tabs having mutually different H values and being aligned in an order that is in accordance with the H values.

The density of the color of a natural tooth visually perceived by humans tends to be determined according to both lightness ($L^*$ value) and chroma ($C^*$ value) in the $L^*a^*b^*$ color system. For example, with colors of natural teeth that have the same hue, there is a tendency for such colors to be perceived as being "dense" if the lightness is low and the chroma is high, and to be perceived as being "pale" if the lightness is high and the chroma is low. For this reason, the density of natural teeth perceived by humans is expressed by an S value that is determined according to to which area, from among areas partitioned by a plurality of straight lines having the predetermined slope k ($0<k$) in the $L^*$-$C^*$ plane ($C^*=\sqrt{\{(a^*)^2+(b^*)^2\}}$), the coordinates of the color of a shade tab in the $L^*a^*b^*$ color system belong. In this way, by classifying the color space of the $L^*a^*b^*$ color system using straight lines having the slope k ($0<k$), classification that is suited to the color identification sense of humans can be performed.

Even within an area of the same S value, if the lightness ($L^*$ value) and the chroma ($C^*$ value) are different, the brightness of colors visually perceived by humans varies. In view of this, the brightness of natural teeth perceived by humans is expressed by a V value that is determined according to to which area, from among areas partitioned by a plurality of straight lines having a predetermined slope m ($0>m$) in the $L^*$-$C^*$ plane, the coordinates of the color of a shade tab in the $L^*a^*b^*$ color system belong. In this way, by classifying the S value areas in the color space using straight lines having the slope m ($0>m$), classification that is suited to the color identification sense of humans can be performed.

The color shade of natural teeth perceived by humans is expressed by an H value that is determined according to to which area, from among areas partitioned by a plurality of straight lines passing through a predetermined reference point in the a*-b* plane, the coordinates of the color of a shade tab in the L*a*b* color system belong. The color shade of natural teeth perceived by humans is, for example, a sense of whether the reddishness is intense or the yellowishness is intense.

In the shade guide according to the present invention, the shade tabs are arranged together in respective S groups, each of which is a shade tab group in which the colors of the shade tabs have a common S value. In other words, shade tabs that have the same density perceived by humans are arranged together in one S group. This enables the observer to compare the density of the colors of the shade tabs included in each S group with the density of the color of the evaluation target tooth, and select the S group that is the closest to the density of the color of the evaluation target tooth. In other words, the observer can determine the density of the color of the evaluation target tooth by selecting the S group that is the closest to the density of the color of the evaluation target tooth.

Furthermore, a plurality of V rows, in each of which a group of shade tabs having a common V value is aligned, are arranged in each S group, and therefore shade tabs having the same brightness perceived by humans are arranged so as to be aligned in one V row. Also, the shade tabs in a V row are aligned in an order that is in accordance with the H values, and therefore in each V row, the shade tabs are aligned in an order that is in accordance with color shades perceived by humans. For this reason, the observer can determine the color shade of the evaluation target tooth by comparing the color shade of the evaluation target tooth and the color shades of the shade tabs included in a certain V row, and selecting the shade tab whose color shade is the closest to the color shade of the evaluation target tooth. Also, the observer can determine the brightness of the evaluation target tooth by comparing the brightness of the evaluation target tooth and the brightnesses of the shade tabs of a plurality of V rows, and selecting the V row whose brightness is the closest to the brightness of the evaluation target tooth. For this reason, with use of the shade guide, the observer can successively discriminate the density, the color shade, and the brightness of the evaluation target tooth. In other words, the shade guide according to the present invention includes shade tabs that are arranged such that the observer can easily discriminate the color of the evaluation target tooth in the order of density, color shade, and brightness. Accordingly, the observer can precisely and easily visually discriminate the color of the evaluation target tooth.

In the shade guide according to the present invention, preferably, in each S group, the plurality of V rows are arranged vertically, and in each V row, the plurality of shade tabs are aligned horizontally.

Accordingly, the observer can more readily visually compare the evaluation target tooth and the shade tabs in a V row in which shade tags having mutually different H values have been aligned horizontally.

In the shade guide according to the present invention, preferably, in each S group, a V row having a reference V value is arranged at the top in the vertical direction.

According to this arrangement, the observer first compares the evaluation target tooth and a group of shade tabs included in the reference V value V row that is arranged at the top. For this reason, when selecting the shade tab that is the closest to the color shade of the evaluation target tooth from the V row, the observer can efficiently select the shade tab that is the closest to the color shade of the evaluation target tooth.

In the shade guide according to the present invention, preferably, in each V row, the plurality of shade tabs are aligned so that a shade tab having a reference H value is arranged in the center, a shade tab whose H value indicates a more intense reddishness than the reference H value is arranged on one side of the shade tab in the center, and a shade tab whose H value indicates a more intense yellowishness than the reference H value is arranged on another side of the shade tab.

According to this arrangement, the observer can first compare the evaluation target tooth and the reference H value shade tab arranged in the center of a V row, and then depending on whether the evaluation target tooth is more reddish or more yellowish than the shade tab in the center, can determine which of the shade tabs on either side of the center is the shade tab that is the closest to the color shade of the evaluation target tooth. Accordingly, the observer can more easily find the shade tab with the closest color shade.

It is preferable for the shade guide according to the present invention to include a base for the arrangement of the plurality of shade tabs, and for the plurality of shade tabs to be able to be removed from the base V row-by-V row and shade tab-by-shade tab.

Accordingly, when selecting an S group, selecting a V row, or selecting the shade tab that is the closest to the color shade of the evaluation target tooth from among the shade tabs in a V row, the observer can retrieve only that V row and bring it close to the evaluation target tooth. Furthermore, the observer can retrieve only the shade tab that has the closest color shade from among V rows, and bring it close to the evaluation target tooth. This improves user-friendliness for when the observer discriminates the color of the evaluation target tooth.

It is preferable for the shade guide according to the present invention to further include a gum-colored part that is gum-colored and has been provided along the bottom of the arranged plurality of shade tabs.

Due to the gum-colored part, the area along the bottom of the shade tabs is caused to be gum-colored, thereby enabling the background of the shade tabs to be gum-colored as well. Since the background of the evaluation target tooth is often gum-colored, causing the background of the shade tabs to be gum-colored as well enables preventing sensory illusions due to the difference in background colors when the observer compares the shade tabs and the evaluation target tooth.

A method for discriminating the color of an evaluation target tooth according to the present invention is a method of discriminating the color of an evaluation target tooth with use of the shade guide of the present invention, the method including: an S value selection step of selecting an S group whose color is closest to the color of the evaluation target tooth by comparing the evaluation target tooth and each S group; an H value selection step of selecting a shade tab whose color is closest to the color of the evaluation target tooth by comparing the evaluation target tooth and each shade tab in one V row among the V rows included in the selected S group; and a V value selection step of selecting a shade tab whose color is closest to the color of the evaluation target tooth by comparing the evaluation target tooth and, in each V row included in the selected S group, the shade tab whose H value is the same as the H value of the shade tab selected in the H value selection step, and the color of the shade tab selected in the V value selection step being discriminated as the color of the evaluation target tooth.

According to the above-described method, the observer first, in the S value selection step, selects the S group that is the closest to the density of the evaluation target tooth, then in the H value selection step, selects a shade tab in one V row whose color shade is the closest to the evaluation target tooth, and then selects, from among the plurality of V rows, the shade tab that has the same color shade as the selected shade tab and that is the closest to the brightness of the evaluation target tooth. Accordingly, the observer compares the evaluation target tooth and the shade tabs in the order of density expressed by S values, then color shade expressed by H values, and then brightness expressed by V values. The sensitivity of human visual perception is thought to be increasingly sensitive in the order of density, then color shade, and then brightness, and therefore by performing the comparisons in this order, the observer can precisely and easily discriminate the color of the evaluation target tooth.

An artificial tooth manufacturing method according to the present invention include the steps of discriminating the color of an evaluation target tooth by the method of the present invention; and manufacturing an artificial tooth based on the color of the shade tab discriminated as the color of the evaluation target tooth.

A set of dental porcelains according to the present invention include pigments that reproduce the colors of the plurality of shade tabs included in the shade guide of the present invention. According to this set of dental porcelains, it is possible to easily reproduce the color of the evaluation target tooth that has been discriminated using the shade guide.

Accordingly, artificial teeth can be manufactured based on the color of a tooth targeted for evaluation that has been precisely discriminated. As a result, an artificial tooth that is close to a desired color is manufactured.

Effects of the Invention

According to the present invention, it is possible to provide a shade guide for precisely and easily visually discriminating the color of a tooth targeted for evaluation.

DESCRIPTION OF THE INVENTION

Figure 1:
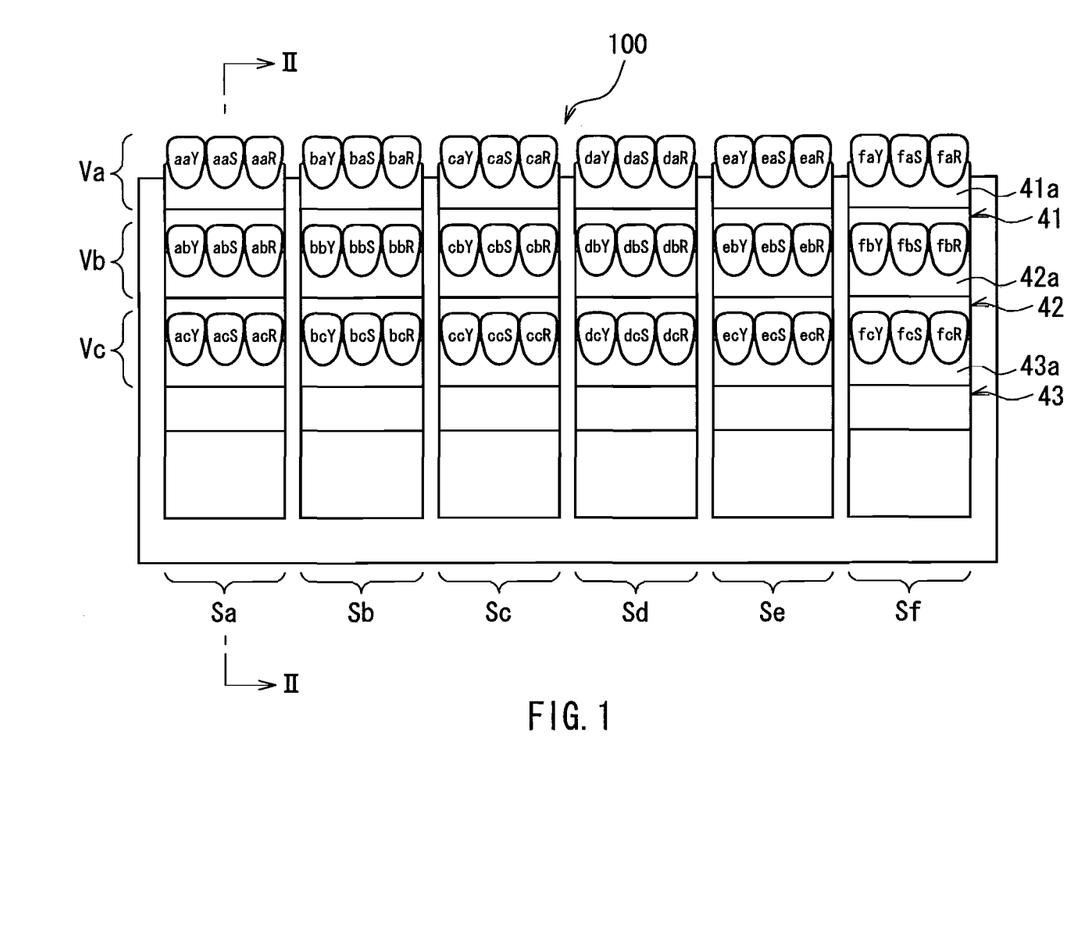
FIG. 1 is a conceptual diagram showing the structure of a shade guide according to an embodiment.

FIG. 1 is a conceptual diagram showing the structure of a shade guide according to the present embodiment. A shade guide 100 shown in FIG. 1 is constituted from a plurality of mutually differently colored shade tabs that are arranged regularly. Although the shade tabs shown in FIG. 1 have numbers such as aaR, aaS, aaY, abR, abS, abY, and so on written thereon, such numbers have been given for the sake of the description, and are not depicted on actual shade tabs.

In the shade guide 100, the shade tabs are arranged together in S groups Sa to Sf. The S groups Sa to Sf are each disposed in a base 10. The S group Sa is constituted from V row units 41 to 43 that are aligned vertically in three levels. Each of the V row units 41 to 43 stores three shade tabs that are aligned horizontally. The shape of the shade tabs is preferably the shape of a human incisor. This is because a shade guide is often used for discriminating the color of an incisor. The relationship between the colors and arrangement of the shade tabs is described later.

In the S group Sa, each of the V row units 41 to 43 includes gum-colored parts 41a to 43a. The gum-colored parts 41a to 43a are gum-colored portions provided below the shade tabs. The shape of the gum-colored parts 41a to 43a is preferably the shape of gums. In other words, if the shade tabs are shaped as incisors, the gum-colored parts 41a to 43a are preferably shaped so as to cover the cervical part of the incisors. Also, a configuration is possible in which only the gum-colored parts 41a to 43a are removable from the V row units. Accordingly, it is possible to replace the gum-colored parts 41a to 43a so as to conform to the color of the gums in the oral cavity targeted for evaluation. Note that such gum-colored parts 41a to 43a are sometimes called a gummy or a gum-colored holder.

Note that the structure of the V row units and shade tabs of the S groups Sb to Sf is the same as the S group Sa.

In the V row (Va) that is the top level in the S groups Sa to Sf, the V row units of the S group Sa to Sf are arranged so as to be aligned on the same horizontal line. Also, in the V row (Vb) that is the second level in the S groups Sa to Sf, and the V row (Vc) that is the third level in the S groups Sa to Sf as well, the V row units are arranged so as to be aligned on the same horizontal lines respectively.

In the S groups Sa to Sf the V row units are structured so that each is removable. Furthermore, in the V row units, the shade tabs are each removable from the V row units.

Figure 2:
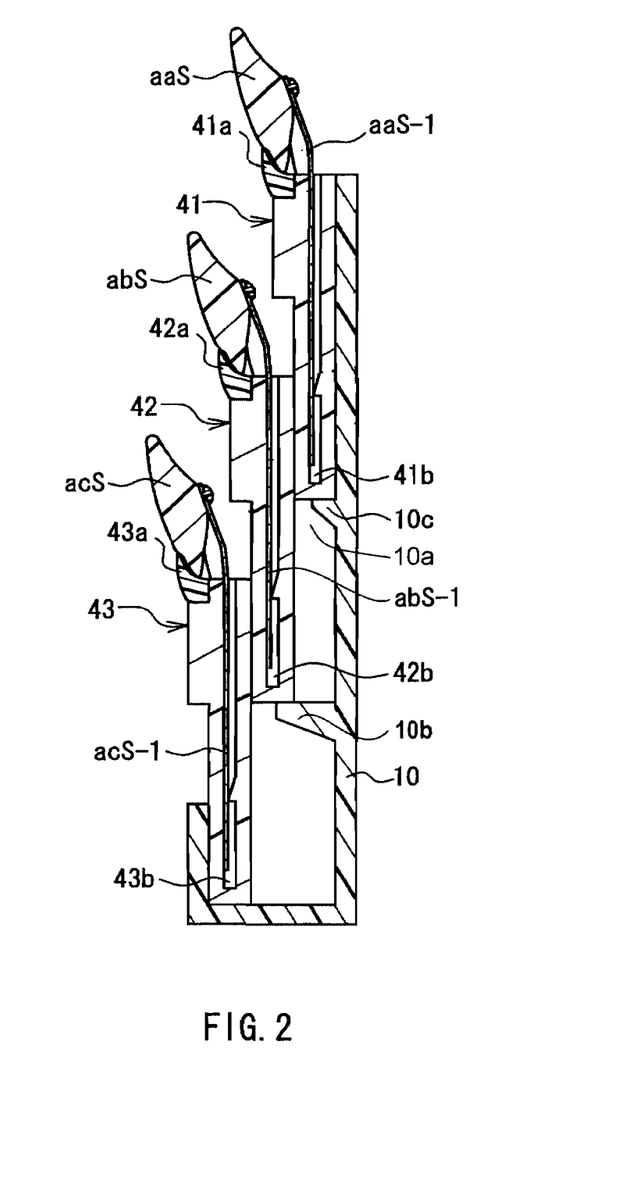
FIG. 2 is a cross-sectional diagram of the shade guide shown in FIG. 1 taken along line II-II.

FIG. 2 is a cross-sectional diagram of the shade guide 100 shown in FIG. 1 taken along line II-II. As shown in FIG. 2, the V row units 41 to 43 that constitute the S group Sa have been inserted into a storage opening 10a of the base 10. The V row units 41 and 42 are supported at mutually different heights by support parts 10c and 10b respectively, which are provided in the storage opening 10a of the base 10. The V row units 41 to 43 have tab insertion openings 41b, 42b, and 43b respectively. Shade tabs aaS, abS, and acS are provided with support plates aaS-1, abS-1, and acS-1, and such support plate aaS-1, abS-1, and acS-1 portions are inserted into the tab insertion openings 41b, 42b, and 43b.

Note that the configuration of the shade guide 100 shown in FIGS. 1 and 2 is an example, and such configuration is not limited to this. For example, each S group can be set in the base as an S group unit, so that each S group is removable. Also, the number of V rows included in one S group, and the number of shade tabs included in one V row are not limited to the example shown in FIG. 1.

Figure 3:
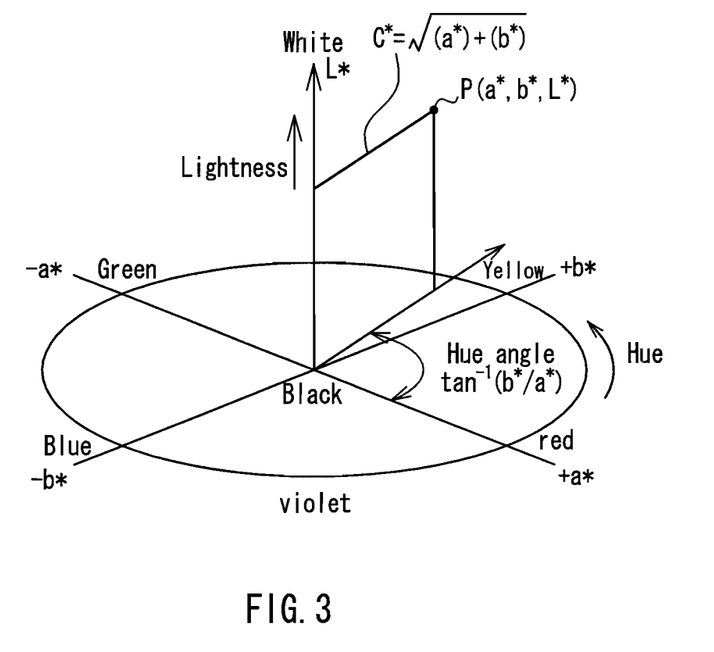
FIG. 3 is a diagram showing an L*a*b* color space.

Next is a description of the relationship between the colors and arrangement of the shade tabs. In the shade guide 100, the shade tabs are regularly arranged based on the colors of the shade tabs. Here, the colors of the shade tabs are expressed by coordinates in the L*a*b* color system. The L*a*b* color system is a color system using the CIE 1976 L*a*b* color space specified in 1976 by the CIE (International Commission on Illumination). FIG. 3 is a diagram showing the L*a*b* color space. The L*a*b* color space is expressed by three-dimensional orthogonal coordinates, namely an L* value, an a* value, and a b* value. The L* value expresses lightness, and the a* value and b* value express chromaticity (properties other than brightness: hue and chroma). The color of each shade tab can be expressed by the three-dimensional coordinates (a*, b*, and L*) of a point p in the L*a*b* color space.

The chroma C* of a color indicated by the point p is expressed by the expression shown below. The higher the chroma, the more vivid the color is, and the lower the chroma, the more dull the color is.

$$C^* = \sqrt{\{(a^*)^2 + (b^*)^2\}}$$

A plane diagram in which the point p is projected on a plane (plane a*-b*) that is perpendicular to the L* axis is called a chromaticity diagram. In the plane a*-b*, +a* expresses the red direction, −a* expresses the green direction, +b* expresses the yellow direction, and −b* expresses the blue direction. As such, the color shade of the color indicated by the point p can be found by observing the chromaticity diagram.

A plane diagram in which the point p is plotted on a plane (plane L*-C*) whose vertical axis is L* and whose horizontal axis is C* is called a color tone diagram. The brightness and vividness of the color indicated by the point p can be found by observing the color tone diagram. Also, the three-dimensional position of the point p in the L*a*b* color space can be found based on the relationship between the color tone diagram and the chromaticity diagram.

Note that the L* value, a* value, and b* value of the color of each shade tab can be measured by a known color measuring device. Since there are cases in which the color of a shade tab is not uniform, there are cases in which the measurement value varies even when the L*, a*, and b* values are measured using the same color measuring device. For this reason, for example, an average value of measurement values obtained by measuring a predetermined position on a shade tab a plurality of times can be specified as the value expressing the color of the shade tab.

Also, the coordinates of the point p in the L*a*b* color space shown in FIG. 3 can be expressed by the lightness L*, the chroma C*, and a hue angle h [$h = \tan^{-1}(b^*/a^*)$]. In this way, the color system expressed using L*C*h is called the L*C*h color system. Although the description below uses the L*a*b* color system as an example of the color system for expressing the colors of the shade tabs in the present embodiment, the color system for expressing the colors of the shade tabs is not limited to this.

Figure 4:
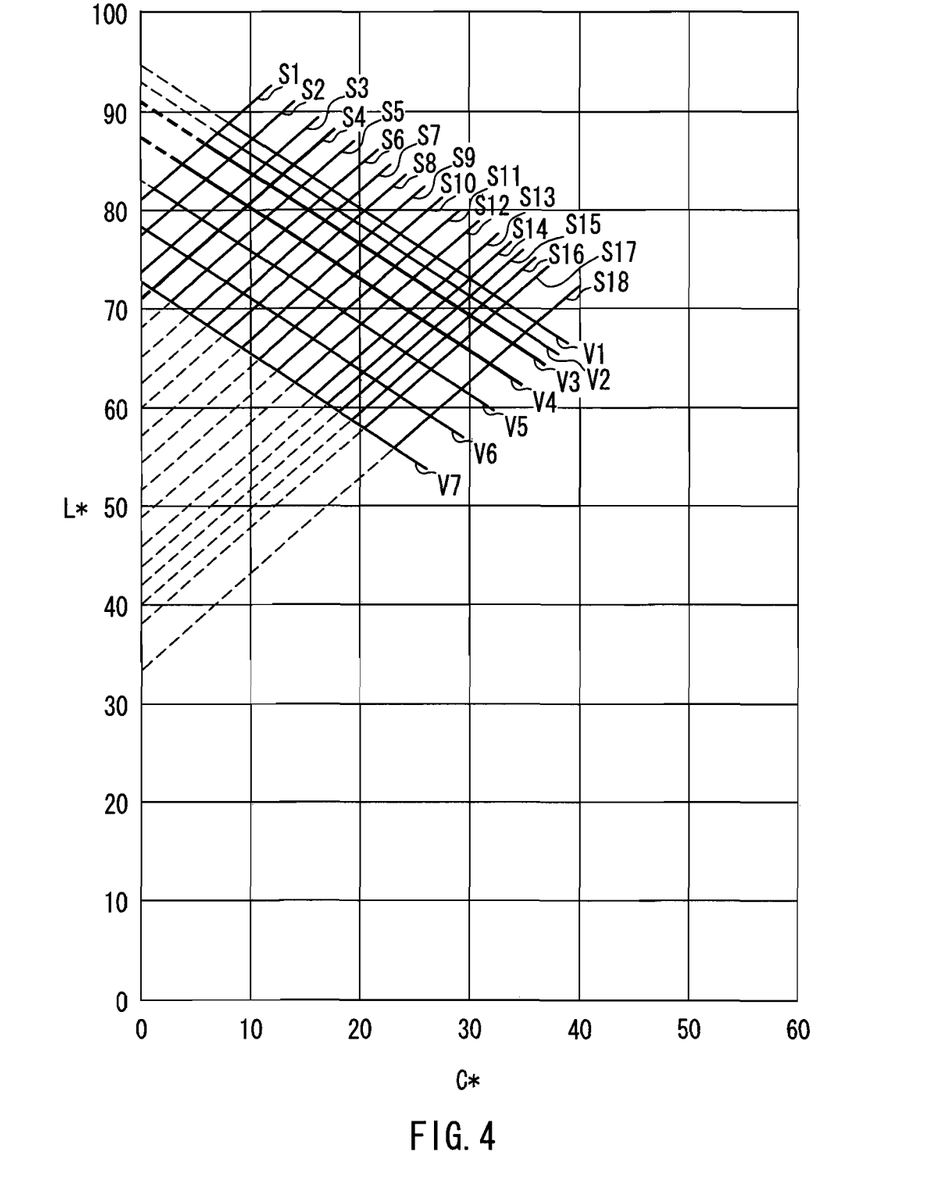
FIG. 4 is an L*-C* plane diagram showing an example of areas for determining S values and V values.

FIG. 4 is an L*-C* plane diagram showing examples of areas for determining the S value and V value of the colors of the shade tabs. In the L*-C* plane diagram shown in FIG. 4, the vertical axis expresses L*, and the horizontal axis expresses C. Straight lines S1 to S18 having a positive slope and straight lines V1 to V7 having a negative slope are depicted in the L*-C* plane diagram shown in FIG. 4.

Also, the slopes and intercepts of the straight lines S1 to S18 can be, for example, empirically obtained based on observation results using existing shade guides or many natural teeth. For example, the straight lines S1 to S18 can be obtained in the following way. First, an experienced observer visually evaluates the color densities of many natural teeth samples using 19 levels of evaluation values. The value of L* and the value of C* are measured for each natural tooth sample, and the color of each natural tooth is plotted on the L*-C* plane. This enables finding out in which sort of areas the teeth of each evaluation value are distributed in the L*-C* plane. In view of this, it is possible to obtain the 18 straight lines expressing the approximate boundaries of 19 areas in which the 19 levels of evaluation values are distributed in the L*-C* plane. These 18 straight lines can be set as the above-described straight lines S1 to S18.

Here, the straight lines S1 to S18 are preferably obtained so as to not be perpendicular to the L axis, but instead have a positive slope as shown in FIG. 4. Accordingly, it is possible to set the S values according to color densities that are sensed by the human eye. Specifically, compared to distinguishing between colors by only differences in lightness, humans tend to more easily distinguish between colors by color densities that are a combination of lightness and chroma. As the color changes diagonally from the upper left to the lower right (as the lightness L* decreases and the chroma C* simultaneously increases) in the L*-C* plane shown in FIG. 4, the color is sensed by humans as having become denser. Humans tend to more easily distinguish between colors by such differences in color density, than distinguish between colors by only differences in color brightness (differences in the case in which L* has changed perpendicularly). For this reason, compared to classifying colors by straight lines that are perpendicular to the L axis, by classifying colors by, for example, straight lines that have a positive slope as shown in FIG. 4, classification can be performed with color densities that are more easily sensed by humans. As the slopes of such straight lines, appropriate values can be calculated based on the distribution of measurement values as described above. Note that although the straight lines S1 to S18 have the same slope in the example shown in FIG. 4, there is no need for such slopes to necessarily be the same.

The S value of the color of each shade tab is determined according to to which area, from among the areas partitioned by the straight lines S1 to S18 in the L*-C* plane diagram shown in FIG. 4, the coordinates of the color of the shade tab belong. Table 1 below shows an example of the relationship between the S values and the areas partitioned by the straight lines S1 to S18. In the example shown Table 1 below, the S value is a value allocated to each area based on a shade number specified by the internationally prevalent VITA Lumin Vacuum shade guide (registered trademark) (hereinafter, called the VITA shade guide). Note that the method of determining the S values is not limited to this.

Also, the S groups Sa to Sf arranged in the shade guide shown in FIG. 1 are each an S group made up of a group of shade tabs that have a common S value. In other words, shade tabs having a common S value are arranged in each of the S groups Sa to Sf.

TABLE 1

| Area | S value |
| --- | --- |
| Between S1 and S2 | −1.5 |
| Between S2 and S3 | −1 |
| Between S3 and S4 | −0.5 |
| Between S4 and S5 | 0.5 |
| Between S5 and S6 | 1 |
| Between S6 and S7 | 1.5 |
| Between S7 and S8 | 2 |
| Between S8 and S9 | 2.5 |
| Between S9 and S10 | 3 |
| Between S10 and S11 | 3.3 |
| Between S11 and S12 | 3.5 |
| Between S12 and S13 | 3.8 |
| Between S13 and S14 | 4 |
| Between S14 and S15 | 4.5 |
| Between S15 and S16 | 5 |
| Between S16 and S17 | 5.5 |
| Between S17 and S18 | 6 |

In the above Table 1, for the colors belonging to the area between the straight line S2 and the straight line S3, S value=−1. For example, shade tabs whose colors have an S value of −1 are arranged in the Sa group shown in FIG. 1.

Specifically, the S values of the nine shade tabs aaY, aaS, aaR, abY, abS, abR, acY, acS, and acR included in the Sa group are all −1. The S values of the shade tab groups arranged in the Sb to Sf groups are as follows: S value=1 (between S5 and S6) in the Sb group, S value=2.5 (between S8 and S9) in the Sc group, S value=3.3 (between S10 and S11) in the Sd group, S value=4 (between S13 and S14) in the Se group, and S value=5.5 (between S16 and S17) in the Sf group.

In this way, a group of shade tabs having a common S value is arranged in each S group. Note that although a group of shade tabs having the same S value is given as an example of a group of shade tabs having a common S value here, a group of shade tabs having a common S value is not limited to this. For example, as a group of shade tabs having a common S value, a group of shade tabs having the same range of S values may be arranged in one S group. For example, the shade tabs may be arranged such that the range of S values of the shade tab group in the Sa group is −1.5 to 0.5 (between S1 and S5), the range of S values in the shade tab group in the Sb group is 1 to 2 (between S5 and S8), the range of S values in the shade tab group in the Sc group is 2.5 to 3 (between S8 and S10), and so on.

Note that the slopes and intercepts of the straight lines S1 to S18 shown in FIG. 4 are as shown in Table 2 below. The values shown in Table 2 below are values that were calculated based on L*, a*, and b* that were measured using the dental colorimeter "ShadeEye" (registered trademark) (hereinafter, called "ShadeEye") manufactured by SHOFU INC. Note that the straight lines S1 to S18 are exemplary, and the straight lines that are the basis of the S groups are not limited to the straight lines S1 to S18.

TABLE 2

|  | Slope | L* intercept |
| --- | --- | --- |
| S1 | 0.967661782 | 81.49670283 |
| S2 | 0.967661782 | 77.75443983 |
| S3 | 0.967661782 | 74.01217683 |
| S4 | 0.967661782 | 71.20547958 |
| S5 | 0.967661782 | 68.39878233 |
| S6 | 0.967661782 | 65.59208508 |
| S7 | 0.967661782 | 62.78538783 |
| S8 | 0.967661782 | 59.97869058 |
| S9 | 0.967661782 | 57.17199333 |
| S10 | 0.967661782 | 54.36529608 |
| S11 | 0.967661782 | 51.55859883 |
| S12 | 0.967661782 | 48.75190158 |
| S13 | 0.967661782 | 45.94520433 |
| S14 | 0.967661782 | 44.07407283 |
| S15 | 0.967661782 | 42.20294133 |
| S16 | 0.967661782 | 40.33180983 |
| S17 | 0.967661782 | 38.46067833 |
| S18 | 0.967661782 | 33.78284958 |

The V value of the color of each shade tab is determined according to to which area, from among the areas partitioned by the straight lines V1 to V7 in the L*-C* plane diagram shown in FIG. 4, the coordinates of the color of the shade tab belong. Table 3 below shows an example of the relationship between the V values and the areas partitioned by the straight lines V1 to V7. Likewise to the straight lines S1 to S18, the slopes and intercepts of the straight lines V1 to V7 can be, for example, empirically obtained based on observation results and color measurement results obtained by an expert using existing shade guides or many natural teeth.

The straight lines V1 to V7 for determining the V values preferably have a negative slope as shown in FIG. 4. This is because in the case in which there is a plurality of colors having the same S value (roughly the same density), and the difference in brightness between such colors is to be distinguished, humans tend to make such a distinguishment according to not only lightness L*, but a combination of lightness L* and chroma C. In other words, in FIG. 4, colors sensed by humans as being dark tend to be plotted in the lower left direction, and colors sensed by humans as being bright tend to be plotted in the upper right direction. These tendencies can be, for example, obtained as the slopes of the straight lines V1 to V7 with use of observation results and color measurement results with respect to many natural teeth as described above.

Also, there is no need for the slopes of the straight lines V1 to V7 to necessarily be the same. In the S groups Sa to Sf in the shade guide shown in FIG. 1, three shade tabs having a common V value are aligned horizontally in a row as one V row, and three of such V rows are arranged vertically.

TABLE 3

| Area | V value |
| --- | --- |
| Between V1 and V2 | 2 |
| Between V2 and V3 | 1 |
| Between V3 and V4 | 0 |
| Between V4 and V5 | −1 |
| Between V5 and V6 | −2 |
| Between V6 and V7 | −3 |

In the example shown in Table 3 above, the V values of colors belonging to the area between the straight lines V3 and V4 are the reference V value "0". Also, in the L*-C* plane diagram, the V value increases when moving in the upward-right direction from the reference V value area, and the V value decreases when moving in the downward-left direction from the reference V value area. Colors belonging to an area in which the V value is large tend to appear bright, and colors belonging to an area in which the V value is small tend to appear dark. In this way, among the areas sandwiched between the straight lines V1 to V7, the area located in the center portion can be set as the reference V value (as one example here, "0") area. In other words, on respective sides of the reference V value area, there is always an area of colors that appear brighter in comparison, and an area of colors that appear darker in comparison.

For example, the shade tabs aaY, aaS, and aaR whose colors have an S value of −1 (between S2 and S3) and a V value that is the reference value "0" (between V3 and V4) are arranged so as to be aligned in the row (Va row) in the top level of the Sa group shown in FIG. 1. In other words, the colors of the shade tabs aaY, aaS, and aaR in the Va row of the Sa group belong to an area enclosed by the straight lines S2, S3, V3, and V4 in the L*-C* plane diagram shown in FIG. 4. The shade tabs abY, abS, and abR whose colors have an S value of −1 and a V value of 2 (colors belonging to an area enclosed by the straight lines S2, S3, V1, and V2) are arranged so as to be aligned in the row (Vb row) in the second level of the Sa group. The shade tabs acY, acS, and acR whose colors have an S value of −1 and a V value of −2 (colors belonging to an area enclosed by the straight lines S2, S3, V5, and V6) are arranged so as to be aligned in the row (Vc row) in the third level of the Sa group. The Va rows, Vb rows, and Vc rows in the other S groups Sb to Sf are also rows in which shade tabs whose colors have V values of 0, 2, and −2 respectively are aligned. In other words, the Va row in the shade guide shown in FIG. 1 is a row of shade tabs having the reference V value. The Vb row is a row of shade tabs whose V value is greater than the reference (shade tabs that appear brighter than the reference), and the Vc row is a row of shade tabs whose V value is less than the reference (shade tabs that appear darker than the reference).

In this way, each of the V rows is an arrangement of shade tabs having a common V value that are aligned horizontally. Note that although a row of shade tabs having the same V value is given as an example of a row of shade tabs having a common V value here, a row of shade tabs having a common V value is not limited to this. For example, as a group of shade tabs having a common V value, a group of shade tabs having the same range of V values may be arranged in one V row. Also, the V value ranges may, for example, overlap between V rows. Also, the relationship between the V values and the arrangement of the V rows is not limited to the above-described example. For example, the arrangement may be such that the V values of the shade tabs in the Va row, the Vb row, and the Vc row are V=0, 2, and −2 respectively, or the arrangement may be such that V=−2, 0, and 2 respectively.

Note that the slopes and intercepts of the straight lines V1 to V7 shown in FIG. 4 are as shown in Table 4 below. The values shown in Table 4 below are values that were calculated based on L*, a*, and b* that were measured using "ShadeEye". Note that the straight lines V1 to V7 are exemplary, and the straight lines that are the basis of the arrangement of the V rows are not limited to the straight lines V1 to V7.

TABLE 4

|    | Slope       | L* intercept |
|----|-------------|--------------|
| V1 | −0.70065259 | 94.15899511  |
| V2 | −0.70065259 | 92.48207433  |
| V3 | −0.70065259 | 90.61804041  |
| V4 | −0.70065259 | 86.86790593  |
| V5 | −0.70065259 | 82.67992668  |
| V6 | −0.70065259 | 77.85950499  |
| V7 | −0.70065259 | 72.30934201  |

Figure 5:
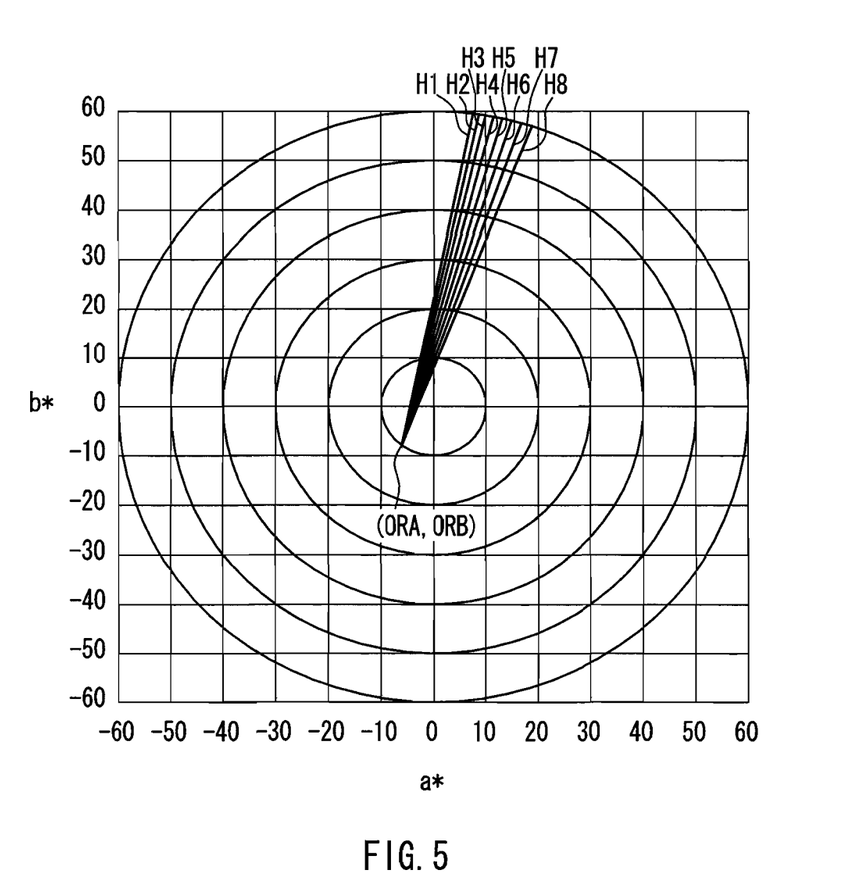
FIG. 5 is an a*-b* plane diagram showing an example of areas for determining H values.

Next is a description of the relationship between colors and the alignment of shade tabs in the V rows. FIG. 5 is an a*-b* plane diagram showing an example of areas for determining H values of shade tab colors. The H value of the color of each shade tab is determined according to to which area, among areas partitioned by straight lines H1 to H8 in the a*-b* plane shown in FIG. 5, the coordinates of the color of the shade tab belong. The straight lines H1 to H8 are a group of straight lines that pass through a reference point (ORA, ORB) and have mutually different slopes. Also, the slopes of the straight lines H1 to H8 can be, for example, empirically obtained based on observation results using existing shade guides or many natural teeth. As one example, first, an experienced observer visually evaluates the color shades of a sample of many natural teeth using 9 levels of evaluation values. The value of a* and the value of b* are measured for each natural tooth sample, and the color of each natural tooth is plotted on the a*-b* plane. This enables finding out in which sort of areas the teeth of each evaluation value are distributed in the a*-b* plane. In view of this, it is possible to obtain the 8 straight lines expressing the approximate boundaries of 9 areas in which the 9 levels of evaluation values are distributed in the a*-b* plane. These 8 straight lines can be set as the above-described straight lines H1 to H8. Note that although the straight lines H1 to H8 all pass through the reference point (ORA, ORB) in the example shown in FIG. 5, there is no need for the all of the straight lines to necessarily pass through the reference point.

Table 5 below shows an example of the relationship between the H values and the areas partitioned by the straight lines H1 to H8. In each V row in the S groups Sa to Sf of the shade guide shown in FIG. 1, the shade tabs are arranged according to the H values. Specifically, in each V row, three shade tabs having a common S value and V value are arranged in order according to H value.

TABLE 5

|                   | H value |
|-------------------|---------|
| Between H1 and H2 | Y3      |
| Between H2 and H3 | Y2      |
| Between H3 and H4 | Y1      |
| Between H4 and H5 | STD     |
| Between H5 and H6 | R1      |
| Between H6 and H7 | R2      |
| Between H7 and H8 | R3      |

In the example shown in Table 5 above, the H value of colors belonging to an area between the straight line H4 and the straight line H5 is a reference H value "STD". In the a*-b* plane, the H value of an area is more yellowish the farther to the left the area is from the area having the reference H value "STD", and the H value of an area is more reddish the farther to the right the area is from the area having the reference H value "STD". In other words, the intensity of yellowness expressed by the H value increases in the order of "Y1", then "Y2", and then "Y3", and the intensity of redness expressed by the H value increases in the order of "R1", then "R2", and then "R3". In this way, among the areas sandwiched between the straight lines H1 to H8, the area located in the center portion can be set as the reference H value (as one example here, "STD") area. In other words, on respective sides of the reference H value area, there is always an area of colors that appear more reddish in comparison, and an area of colors that appear more yellowish in comparison.

For example, in the Va row in the Sa group of the shade guide shown in FIG. 1, it can be considered that the H value of the shade tab aaY is "Y3", the H value of the shade tab aaS is "STD", and the H value of the shade tab aaR is "R3". Likewise to the Va row, the H values of the shade tabs abY, abS, and abR in the Vb row in the Sa group can be considered to be "Y3", "STD", and "R3" respectively, in the stated order from the left. Also, likewise, the H values of the acY, acS, and acR shade tabs in the Vc row in the Sa group can be considered to be "Y3", "STD", and "R3" respectively. In this case, in the Sa group, the H values of the shade tabs aaY, abY, and acY that are arranged so as to be aligned on the same vertical line are all "Y3", the H values of the shade tabs aaS, abS, and acS are all "STD", and the H values of the shade tabs aaR, abR, and abR, are all "R3". In other words, shade tabs having a common H value are arranged so as to be aligned on the same vertical line.

The H values of the shade tabs in the Va rows, the Vb rows, and the Vc rows of the other S groups Sb to Sf can also be arranged in the same way as Sa. Specifically, in each V row in the S groups, a shade tab having the reference H value is arranged in the center, a shade tab having an H value that is more reddish than the reference is arranged on the right, and a shade tab whose H value is more yellowish than the reference is arranged on the left. The H values of the shade tabs in the above-described V rows are exemplary, and are not limited to these. Also, the relationship between the H values and the arrangements of the shade tabs in the V rows is not limited to the above-described example. For example, arranging may be performed so that the H values of the three shade tabs included in each V row are "R3", "STD", and "Y3" in order from the left.

Note that the slopes and intercepts of the straight lines H1 to H8 shown in FIG. 5 are as shown in Table 6 below. Also, the coordinates of the reference point (ORA, ORB) shown in FIG. 5 are as shown in Table 7 below. The values shown in Table 6 and Table 7 below are values that were calculated based on L*, a*, and b* that were measured using "Shade-Eye". Note that the straight lines H1 to H8 are exemplary, and the straight lines that are the basis of the shade tab arrangement in the V rows are not limited to the straight lines H1 to H8.

TABLE 6

|    | Slope       | b* intercept |
|----|-------------|--------------|
| H1 | 5.22784113  | 20.81705554  |
| H2 | 4.730478616 | 18.01077045  |
| H3 | 4.292415324 | 15.53907134  |
| H4 | 3.902007598 | 13.33626081  |
| H5 | 3.550400203 | 11.35237468  |
| H6 | 3.230731215 | 9.548695698  |
| H7 | 2.937593547 | 7.894715267  |
| H8 | 2.666661311 | 6.366025279  |

TABLE 7

| ORA | −5.75  |
|-----|--------|
| ORB | −7.904 |

By performing arranging based on the colors of the shade tabs as described above, a group of shade tabs having a common S value is arranged in each S group. Therefore, a group of shade tabs having the same "density" that can be perceived by the observer is arranged in each S group. In each S group, V rows, in each of which shade tabs having a common V value are aligned horizontally, are arranged vertically in three levels. Among the three levels of V rows, the top level is a row of shade tabs having the reference V value, the second level is a row of shade tabs whose V value is greater than the reference V value, and the third level is a row of shade tabs whose V value is less than the reference V value. For this reason, a row of shade tabs whose colors have a reference brightness is arranged in the top level (Va row), a row of shade tabs whose colors appear brighter than the reference is arranged in the second level (Vb row), and a row of shade tabs whose colors appear darker than the reference is arranged in the third level (Vc row). Also, in each V row, a shade tab having the reference H value is arranged in the center, a shade tab having an H value that is more reddish than the reference is arranged on the right, and a shade tab whose H value is more yellowish than the reference is arranged on the left. For this reason, in each V row, a shade tab having a reference color shade is arranged in the center, a shade tab that is reddish is arranged on the right, and a shade tab that is yellowish is arranged on the left.

Figure 6A:
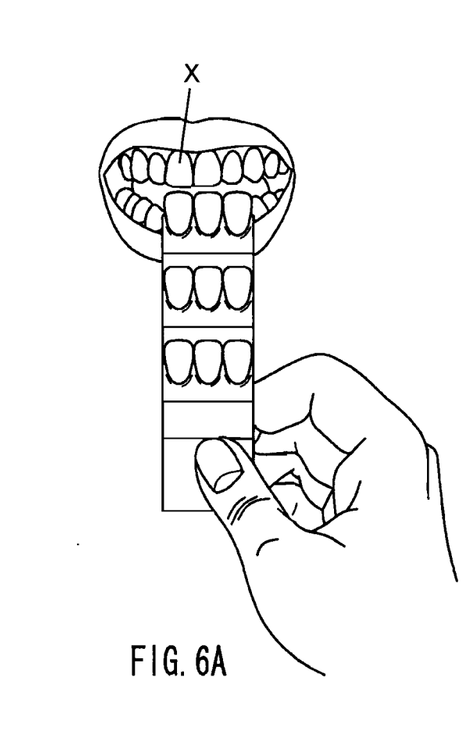
FIG. 6A is a diagrams for illustrating a method of discriminating the color of a tooth targeted for evaluation with use of a shade guide 100.
Figure 6B:
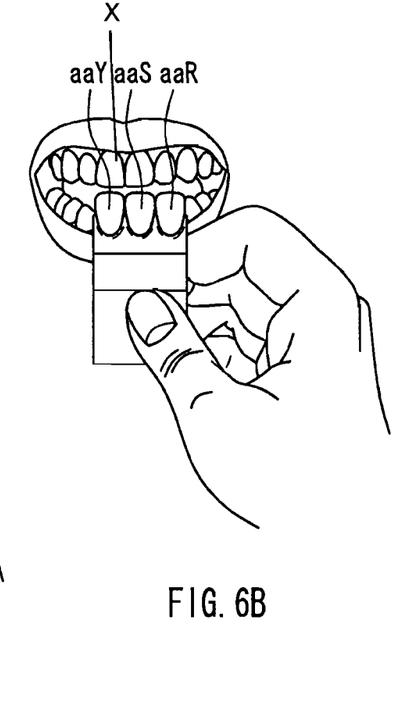
FIG. 6B is a diagram for illustrating a case of performing a comparison with a V row unit in a top level of a shade guide 100.
Figure 6C:
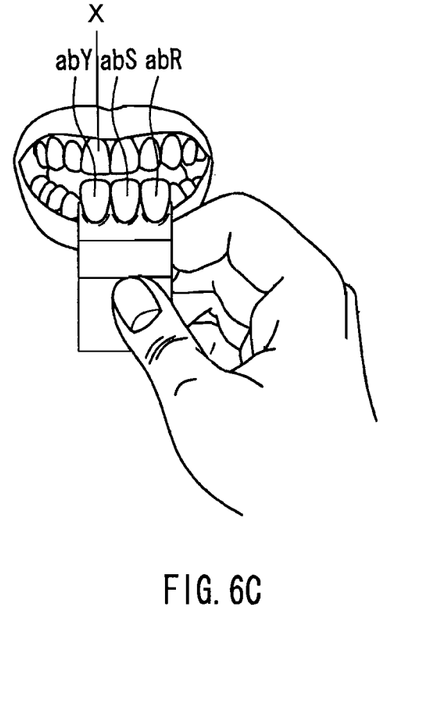
FIG. 6C is a diagram for illustrating a case of performing a comparison with a V row unit in a next lower level of a shade guide 100.

Next is a description of an exemplary method for discriminating the color of a tooth targeted for evaluation with use of the shade guide 100 shown in FIG. 1, with reference to FIGS. 6A-6C. First, the observer retrieves, from the base 10, the V row units of any one of the S groups among the S groups Sa to Sf, and as shown in FIG. 6A, brings the retrieved V row units close to an evaluation target tooth X. The observer visually compares the density of the color of the evaluation target tooth X and the densities of the colors of the shade tabs arranged in the retrieved S group. The observer performs such operation for each of Sa to Sf, and selects the S group whose colors are closest to the density of the color of the evaluation target tooth X. Such operation can be performed because a group of shade tabs having a common S value, that is to say, a group of shade tabs having the same density is arranged in each of the S groups. Also, the observer can easily select an S group since, regarding human visual sensitivity, sensitivity with respect to distinguishing between such S values is thought to be the most superior.

Note that the visual comparison of the shade tabs and the evaluation target tooth X is preferably always performed under the same conditions. For example, conditions such as the illumination, lighting method, and the visual angle and position of the observer when comparing may be determined in advance, and the observer may always compare the shade tabs and the evaluation target tooth X under such conditions. This enables suppressing variations between evaluation results due to changes in the conditions.

Also, although it is preferable for the observer to compare the evaluation target tooth and the shade tabs by direct viewing, it is possible to, for example, look at the shade tabs and an evaluation target tooth captured in a photograph, image, or the like, and compare the colors thereof.

Also, instead of retrieving each S group from the base 10 and performing the comparison as shown in FIG. 6A, the observer may bring the shade guide 100 close to the evaluation target tooth X and slide the shade guide 100 horizontally with respect to the evaluation target tooth, thus performing the comparison by successively bringing the S groups Sa to Sf close to the evaluation target tooth X.

Upon selecting an S group, the observer next retrieves the V row unit in the top level of the selected S group, and as shown in FIG. 6B, brings the V row unit close to the evaluation target tooth X. FIG. 6B shows, as an example, the case of performing a comparison with the V row unit (including the shade tabs aaY, aaS, and aaR) in the top level (Va row) of the Sa group. The observer visually compares the color shade of the evaluation target tooth X and the color shades of each of the shade tabs aaY, aaS, and aaR arranged in the retrieved V row unit, and selects the shade tab whose color shade is the closest to the evaluation target tooth X. As described above, in each V row, a shade tab having the reference color shade (in the example shown in FIG. 6B, aaS) is arranged in the center, a shade tab that is yellowish (aaY) is arranged on the right, and a shade tab that is reddish (aaR) is arranged on the left. For this reason, by merely bringing the V row unit close to the evaluation target tooth X and looking, the observer can swiftly determine whether the color shade of the evaluation target tooth X is more reddish than the reference, more yellowish than the reference, or roughly the same as the reference. As one example, the following describes the case in which the shade tab aaY whose color shade is yellowish has been selected as the shade tab whose color shade is the closest to the evaluation target tooth X.

Upon selecting the shade tab aaY, the observer next retrieves the V row unit in the next lower level of the Sa group, that is to say, the V row unit in the Vb row, and as shown in FIG. 6C, brings the V row unit close to the evaluation target tooth X, and performs a comparison with the shade tab abY whose color shade is yellowish. Next, the observer retrieves the V row unit that is another level down, that is to say, the V row unit in the Vc row, brings the V row unit close to the evaluation target tooth X, and performs a comparison with the shade tab acY. As described above, the three levels of V rows (Va row, Vb, Vc row) in each S group are arranged from the top in the order of the color having the reference brightness, then the color brighter than the reference, and then the color darker than the reference, and therefore by retrieving the V row units in order from the top level to the bottom level and performing comparisons, the observer can perform the comparisons in the order of the reference shade tab, then the shade tab whose color is brighter, and then the shade tab whose color is darker. Through this operation, the observer selects the shade tab whose brightness is the closest to the evaluation target tooth X.

Note that instead of retrieving the V row units in order from the top and performing the comparisons as described above, the observer may retrieve the three shade tabs aaY, abY, and acY having the selected color shade from the V rows, insert them into a unit, bring such unit close to the evaluation target tooth X, and perform a comparison. This enables selecting, from among the shade tabs aaY, abY, and acY having the selected color shade, the shade tab whose brightness is the closest to the evaluation target tooth X. Note that as described above, shade tabs having a common H value (whose color shades are the same) are arranged vertically on the same line in each S group, and therefore the observer can easily know the arrangement location of shade tabs whose color shade is the same as the shade tab having the selected color shade.

The shade tab whose color is the closest to the evaluation target tooth X is selected through the above operation. In other words, the shade tab whose color is the closest to the evaluation target tooth X is discriminated. According to this method, the observer can narrow down the shade tabs whose colors are close to the evaluation target tooth, in the order of density, then color shade, and then brightness. It is therefore possible to efficiently discriminate shade tabs whose colors are close to the evaluation target tooth using a natural sense that is suited to the human sense of sight.

Figure 7:
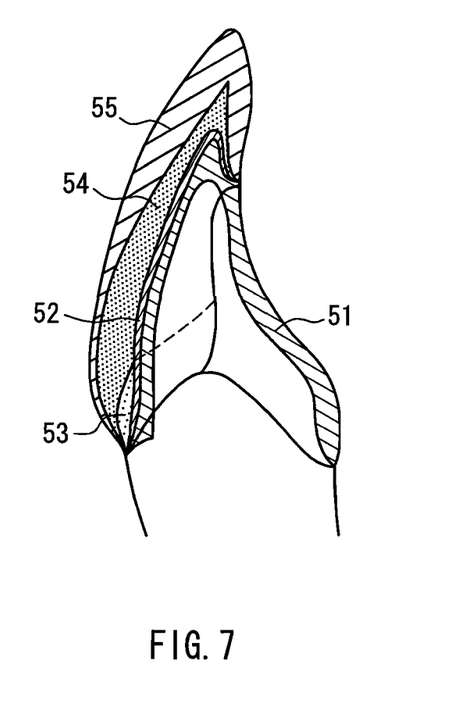
FIG. 7 is a cross-sectional diagram of an MC crown.

Next is a description of steps for manufacturing an artificial tooth based on the color of a shade tab discriminated using the discrimination method described above. As one example, the following describes steps for manufacturing a metal ceramic crown (hereinafter, called an MC crown) that is the same color as the color of the shade tab. An MC crown is manufactured by laminating a plurality of mutually different colored ceramic (porcelain) layers onto a center part formed from metal. FIG. 7 is a cross-sectional diagram of an MC crown. The MC crown shown in FIG. 7 is formed by laminating an opaque porcelain layer 52 that is opaque, an opaque dentin layer 53 (or a cervical layer), a dentin layer 54, and an enamel layer 55 on a metal 51.

In the steps for manufacturing the MC crown shown in FIG. 7, a manufacturer selects the materials to be used as the opaque porcelain layer 52, the opaque dentin layer 53, the dentin layer 54, and the enamel layer 55, and manually forms each of these layers. When selecting the materials of the layers, it is necessary for the manufacturer to select materials that are appropriately colored in order to reproduce the color of the shade tab. For example, by preparing in advance data (hereinafter, called a recipe) that records, in association with each other, numbers for specifying the color of each shade tab, and information indicating materials for reproducing such colors in an artificial tooth, the manufacturing can known which materials enable reproducing the color of the selected shade tab by referencing the recipe. The recipe records, for example, various types of porcelain materials used as the materials of the layers, and mixing ratios thereof.

In this way, with reference to the recipe, the manufacturer selects porcelain materials for reproducing the color of the shade tab discriminated using the discrimination method described above, and forms the opaque porcelain layer 52, the opaque dentin layer 53, the dentin layer 54, and the enamel layer 55 with use of the selected porcelain materials. This enables easily reproducing the color of the shade tab.

The porcelain materials of the layers are examples of dental porcelains, and are porcelains in which glass is used as the body, and at least one of a color pigment, a phosphor material, and an opaque material are added as a pigment. For this reason, the color of the artificial tooth is determined according to the mixing ratio of the pigments such as the color pigment, the phosphor material, and the opaque material included in the porcelain materials of the layers forming the artificial tooth. In view of this, by preparing, for each shade tab, the porcelain materials of the layers that include pigments for reproducing the color of the shade tab, along with the recipe, the manufacturer can quickly obtain materials that reproduce the color of the shade tab selected using the shade guide.

Note that in order to obtain the mixing ratio of pigments in the porcelain materials of the layers that reproduces the color of the shade tab, it is necessary to, for example, perform trial and error by repeatedly creating sample MC crowns using various porcelain materials. At this time, the manufacturer can make the determination of whether the color of a sample MC crown reproduces a desired color by, for example, visually comparing the shade tab and the sample MC crown. Also, the manufacturer can make such determination by measuring the color of the sample MC crown using the ShadeEye described above.

The glass that is the body of the porcelain materials can be obtained by preparing, for example, silica, alumina, potassium carbonate, sodium carbonate, lithium carbonate, calcium carbonate, and magnesium oxide. A porcelain material is obtained by mixing at least one of, for example, a color pigment, a phosphor material, and an opaque material in this glass body. Examples of the color pigment include cobalt oxide, nickel oxide, and manganese oxide. Examples of the phosphor material include lanthanum oxide and yttrium oxide. Examples of the opaque material include tin oxide and zirconium oxide. Note that the raw material of the glass body, the color pigment, the phosphor material, and the opaque material are not limited to the examples described above.

The manufacturer builds up a porcelain material on the metal 51 using a build-up brush, and performs baking using a porcelain baking vacuum electric furnace. Thus, a porcelain layer is formed. This operation is repeated each time the manufacturer forms the opaque porcelain layer 52, the opaque dentin layer 53, the dentin layer 54, and the enamel layer 55.

Note that the MC crown shown in FIG. 7 is an example, and the structure of the MC crown is not limited to the MC crown shown in FIG. 7. Also, the artificial tooth that can be manufactured based on the color of the shade tab is not limited to an MC crown. Examples of artificial teeth targeted for manufacturing also include an all-ceramic crown (AC crown), a crown having a structure in which resin is built up on metal, and a crown having a structure in which resin is built up on ceramic. The artificial tooth targeted for manufacturing is not limited to a crown, and examples also include an inlay, an onlay, a bridge, and an implant superstructure.

INDUSTRIAL APPLICABILITY

The present invention is useful as a shade guide that improves reliability and efficiency in discriminating the color of a tooth.

What is claimed is:
1. A shade guide comprising:
a plurality of support plates, each of the support plates detachably carrying a plurality of shade tabs having mutually different colors as a single row;
a base having bottom, front and rear walls and an open top, removably supporting the plurality of support plates at a plurality of heights and in adjacent relationships to define a plurality of column groups of the shade tabs, each of the column groups comprising plural support plates positioned at different heights, the shade tabs of each of the column groups being arranged in a plurality of horizontal rows and a plurality of vertical individual columns;

wherein the plurality of shade tabs are arranged in a pattern determined by:
- S values assigned, respectively, to a plurality of first straight lines having a predetermined slope k (0<k) in an L*-C* plane in an L*a*b* color system;
- V values assigned, respectively, to a plurality of second straight lines having a predetermined slope m (0>m) in the L*-C* plane, such that the first straight lines and the second straight lines intersect each other; and
- H values assigned, respectively, to a plurality of third straight lines in an a*-b* plane in the L*a*b* color system;

wherein the plurality of column groups are separated based on the S values such that each column group includes shade tabs within a common fixed range of S values;

wherein the plurality of rows are separated based on the V values such that each row includes shade tabs within a common fixed range of V values; and wherein the plurality of individual columns are separated based on the H values such that each individual column includes shade tabs within a common fixed range of H values, wherein in each column group, the support plate with shade tabs having a reference V value is arranged at the uppermost row, and wherein in each column group and in each row, the plurality of shade tabs are arranged so that a shade tab having a reference H value is arranged in the center, a shade tab whose H value indicates a more intense reddishness than the reference H value is arranged on one side of the shade tab in the center, and a shade tab whose H value indicates a more intense yellowishness than the reference H value is arranged on another side of the shade tab in the center.

2. The shade guide according to claim 1, further comprising a gum-colored part provided along the bottom of the arranged plurality of shade tabs.

3. A method of determining the color of an evaluation target tooth with the use of the shade guide according to claim 1, the method comprising:
- an S value selection step of selecting one column group whose color is closest to the color of the evaluation target tooth by comparing the evaluation target tooth and the shade tabs in said one column group;
- an H value selection step of selecting one individual column whose color is closest to the color of the evaluation target tooth by comparing the evaluation target tooth and the shade tabs in one individual column among the individual columns included in the selected column group; and
- a V value selection step of selecting a shade tab whose color is closest to the color of the evaluation target tooth by comparing the evaluation target tooth and the shade tabs included in the selected one individual column, the color of the shade tab selected in the V value selection step being determined as the color of the evaluation target tooth.

* * * * *